(12) United States Patent
Gonopolskiy et al.

(10) Patent No.: US 8,504,130 B2
(45) Date of Patent: Aug. 6, 2013

(54) NON-INTERFERING PHYSIOLOGICAL SENSOR SYSTEM

(75) Inventors: Oleg Gonopolskiy, West Bloomfield, MI (US); Ronald A. Widman, Macomb, MI (US); Arik Anderson, Birmingham, MI (US)

(73) Assignee: Covidien LP, Boulder, CO (US)

( * ) Notice: Subject to any disclaimer, the term of this patent is extended or adjusted under 35 U.S.C. 154(b) by 997 days.

(21) Appl. No.: 12/543,362

(22) Filed: Aug. 18, 2009

(65) Prior Publication Data
US 2010/0087718 A1 Apr. 8, 2010

Related U.S. Application Data

(60) Provisional application No. 61/103,317, filed on Oct. 7, 2008.

(51) Int. Cl.
*A61B 5/1455* (2006.01)
(52) U.S. Cl.
USPC .............. 600/336; 600/310; 600/323
(58) Field of Classification Search
USPC ............ 600/310, 322, 323, 330, 336, 340, 600/344, 473, 476; 356/41; 702/19
See application file for complete search history.

(56) References Cited

U.S. PATENT DOCUMENTS

| 5,255,202 A | * | 10/1993 | Kido et al. | 702/190 |
| 5,490,505 A | * | 2/1996 | Diab et al. | 600/323 |
| 5,873,821 A | * | 2/1999 | Chance et al. | 600/310 |
| 6,397,092 B1 | * | 5/2002 | Norris et al. | 600/323 |
| 2004/0034294 A1 | * | 2/2004 | Kimball et al. | 600/323 |

* cited by examiner

*Primary Examiner* — Eric Winakur
*Assistant Examiner* — Chu Chuan (JJ) Liu
(74) *Attorney, Agent, or Firm* — Harness, Dickey & Pierce, P.L.C.

(57) ABSTRACT

A system includes a light source, a photodetector in optical communication with the light source, and a processor in communication with said photodetector and configured to output a signal representing oxygen saturation independent of an interfering signal from an interfering source. The system may further include an analog-to-digital converter in communication with the processor that is configured to digitize a signal from the photodetector by oversampling and output oversampling data to the processor. The processor may include an averaging filter that averages the oversampling data received from said analog-to-digital converter prior to decimation to generate an oversampling number.

18 Claims, 5 Drawing Sheets

FIG. 7

NON-INTERFERING PHYSIOLOGICAL SENSOR SYSTEM

CROSS-REFERENCE TO RELATED APPLICATIONS

This application claims priority to U.S. Ser. No. 61/103,317 filed on Oct. 7, 2008, which is incorporated herein by reference in its entirety.

BACKGROUND

Pulse oximeters and tissue oximeters are medical devices that measure absorption of near infrared light to determine blood oxygen saturation. Sometimes, pulse oximeters and tissue oximeters are used simultaneously on a patient's body. Typically, pulse oximeters use a disposable sensor placed on a peripheral site of the body where arterial capillary blood pulsation is high, such as on the finger. The sensor uses one or more light emitting diodes (LEDs) to emit light with two wavelengths and silicon photodetectors to measure light intensity transmitted through or reflected back from the site. To separate the two wavelengths of light, pulse oximeters usually use a single frequency to excite each LED in two different phases shifted by 180 degrees. By analyzing the AC of the reflected light intensities at two different wavelengths separately, pulse oximeters estimate arterial blood oxygen saturation (aSpO2). Because the arterial blood has uniform oxygen saturation across the whole body, a single sensor is usually employed on the patient to measure arterial blood oxygen saturation.

Tissue oximeters, including a cerebral oximeter, analyze the DC components of the reflected light at multiple wavelengths to determine oxygen saturation. Tissue oximeter sensors employs light from one or more LEDs or laser diodes and uses silicon photodiodes, avalanche photodiodes, or similar detectors to measure light absorption. In order to measure absorption of the light that travels deep inside the tissue or organs, tissue oximeters use a large separation between emitters and detectors. The measured light absorption related to the oxygen status of the tissue or organs is called the regional oxygen saturation (rSO2). Because different sites of the body have different values of regional oxygen saturation, multiple sensors on multiple body locations are usually employed to measure patient status. To measure light intensity with a high signal to noise ratio, the tissue oximeter employs a synchronous demodulation technique. To separate light signals from multiple wavelengths and from multiple sensors, tissue oximeters use time division or frequency division multiplexing or similar methods Because both pulse and tissue oximeters use near infrared light, light generated by one type of oximeter can interfere with the other type of oximeter. This interference can happen regardless of where the sensors are placed on the patient's body. For example, light from one sensor can be detected by the light detectors of another sensor by: (1) propagating directly inside the tissue, (2) exiting from the tissue under the sensor and reflecting from objects surrounding the patient back to the tissue. Interference may be especially common during infant or pediatric monitoring where, for example, a forehead reflectance pulse oximeter sensor and cerebral oximeter sensor are used in close proximity.

Pulse oximeters and tissue oximeters, however, do not use continuous sinusoidal signals for modulation-demodulation. Rather, pulse and tissue oximeters use pulses with spectrums that may include multiple harmonics of a fundamental frequency. The harmonics of the fundamental frequency of one oximeter can fall in a pass band of a demodulator of another oximeter creating interference.

The severity of interference may depend upon differences between the modulation frequencies of the oximeters, a width of the pulses, and the pass band of a filter of the demodulator. The pulse oximeter may be configured to reject multiple harmonics of an AC component of ambient light and/or a main power line. The modulation frequency $f_1$ of the pulse oximeter may be related to the frequency of the main power line (e.g., 50 Hz or 60 Hz). For example, the modulation frequency $f_1$ may be equal to 1365 Hz so that differences between the modulation frequency $f_1$ and the 22nd harmonic of ambient light having a frequency of 60 Hz (i.e., 1365−22*60 Hz=45 Hz) will not fall inside the pass band of the demodulator that usually is equal to the band frequency of plethysmogram (e.g., F=7.5 Hz).

However, light pulses from the pulse oximeter at a frequency (e.g., $f_1$) of, for example, 1365 Hz may be received by and interfere with the tissue oximeter sensor. In particular, the light pulses may interfere with the tissue oximeter sensor light pulses depending on modulation frequency (e.g., $f_2$) of the tissue oximeter pulses.

Because of low light return in the tissue oximeter sensor in comparison to the pulse oximeter sensor, the duration of the light pulses used for the tissue oximeter may be much more than for the pulse oximeter (e.g., $f_2$ is less than $f_1$). For example, the modulation frequency $f_2$ of the tissue oximeter pulses may be 15 Hz with a pulse duration of 1 millisecond while the frequency $f_1$ of the light pulses from the pulse oximeter may be 1365 Hz. The tissue oximeter may use a synchronous demodulator to multiply the signal from the photodiode by +1 or −1 depending on a phase of the light source excitation. Because of this, the synchronous filter may successively demodulate all harmonics of the modulation frequency $f_2$. We can see that the $91^{st}$ harmonic of the tissue oximeter will interfere with the pulse oximeter (e.g., 15 Hz*91=1365 Hz). Thus, a pulse oximeter signal at 1365 Hz will be demodulated by the tissue oximeter as a DC signal. In practice because the interfering frequency $f_i$ is subject of the slight variation from 15 Hz*91 due to low frequency fluctuations of the system clock of the pulse oximeter CPU, the DC surplus from the interfering light will show signs of low frequency variations. In some cases these low frequency variations can be significant and erroneously interpreted as a physiological effect.

Interference may occur with other values of $f_1$ and $f_2$, and separation of $f_1$ and $f_2$ does not assure absence of interference between two oximeters. Accordingly, a new system is needed that eliminates interference.

DETAILED DESCRIPTION

An exemplary system includes a light source in optical communication with at least one photodetector. A processor is configured to output a signal indicative of oxygen saturation. The signal representing oxygen saturation is independent of an interfering signal from an interfering sensor. In one exemplary approach, each light source may be modulated and demodulated with precise sinusoidal signals that have different frequencies relative to the other light sources. Demodulation may be used to extract signals that represent tissue light attenuations from, for example, a tissue oximeter, with high precision. Various implementations of detecting and removing interference are discussed herein. The system may include any number of sensors or light generating devices, including but not limited to, a pulse oximeter sensor or a tissue oximeter sensor.

Figure 1:
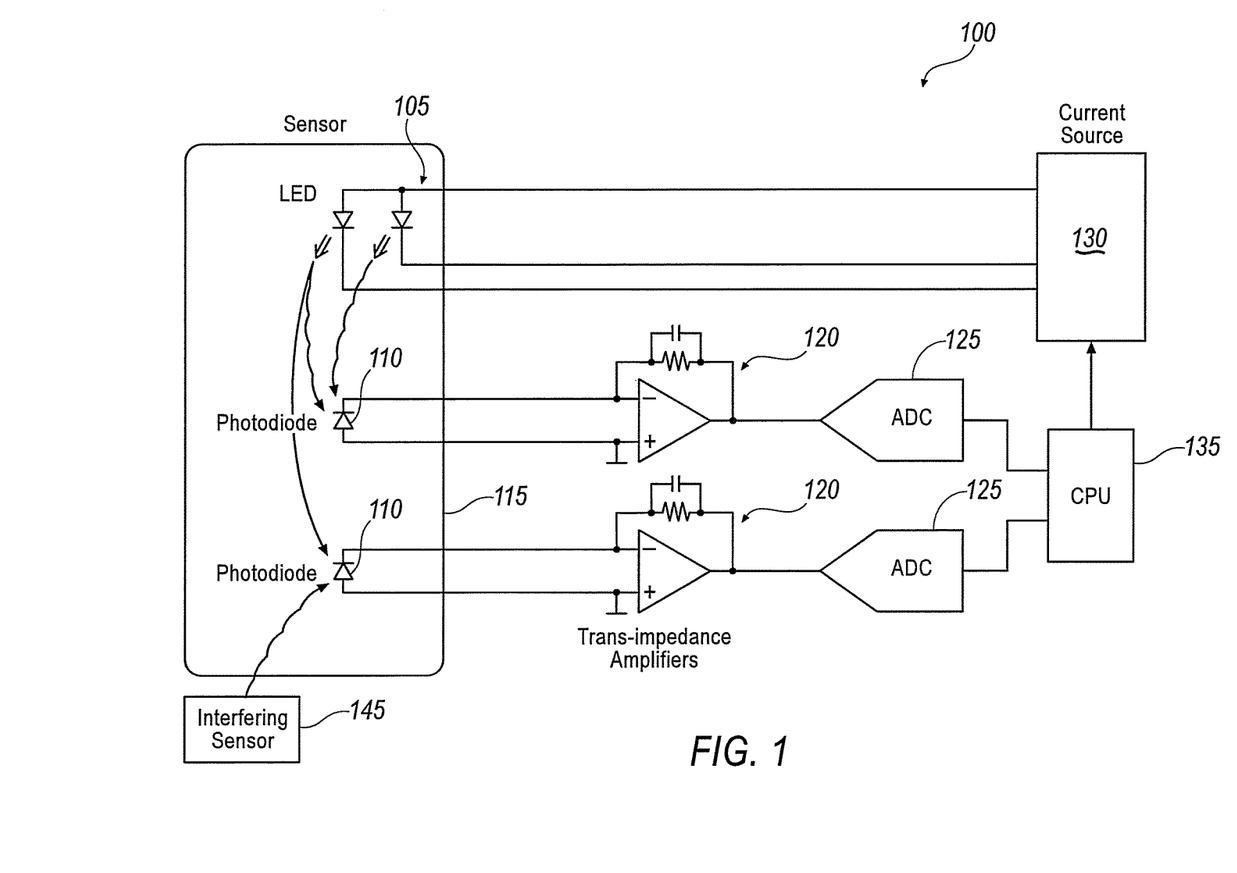
FIG. 1 is a system diagram of an exemplary tissue oximeter sensor configured to reduce interference from an interfering sensor.

FIG. 1 is a system diagram of an exemplary tissue oximeter 100 configured to remove interference from an interfering sensor 145. The tissue oximeter 100 may include one or more light sources 105 and one or more photodetectors 110 disposed on one or more sensor pads 115. The tissue oximeter 100 may further include at least one trans-impedance amplifier 120 for each photodetector 110, at least one analog-to-digital converter (ADC) 125 for each photodiode, a current source 130, and at least one processor 135.

The light sources 105 may include one or more light emitting diodes (LEDs) configured to transmit light at a predetermined frequency. For example, the light source 105 may be configured to transmit light in the near-infrared region of the electromagnetic spectrum.

The photodetectors 110 may each be in optical communication with at least one of the light sources 105 and configured to receive light with a specific wavelength, such as light in the near-infrared region of the electromagnetic spectrum. Each photodetector 110 may include, for example, one or more photodiodes.

The trans-impedance amplifiers 120 are each electrically connected to at least one of the photodetectors 110. The trans-impedance amplifier 120 may include an operational amplifier connected to the photodetector 110 and a resistor electrically connected to one input of the operational amplifier and to the output of the operational amplifier. The trans-impedance amplifier 120 may be configured to receive current from the photodetector 110 and convert the current into a voltage.

The analog-to-digital converters 125 may each be in communication with one or more trans-impedance amplifiers 120. The analog-to-digital converters 125 are configured to convert the analog voltage generated by the trans-impedance amplifier 120 into a digital signal. The digital output of the analog-to-digital converter 125 may represent a magnitude of the voltage output by the trans-impedance amplifier 120. The analog-to-digital converter 125 may be configured to digitize the signal from the photodetector 110 by oversampling to generate oversampling data.

The current source 130 may be in communication with the light sources 105 and provide one or more of the light sources 105 with current so that the light sources 105 may generate light. One or more current sources 130 may be used, and the current output by the current source 130 may depend upon the light source 105.

The processor 135 is in communication with the analog-to-digital converters 125 and the current source 130 and may include a central processing unit (CPU) configured to execute computer programs. The processor 135 may be configured to receive the digital output from the analog-to-digital converter 125 (e.g., the oversampling data), as well as control the current source 130 to adjust the amount of current provided to the light sources 105. The processor 135 may further be configured to demodulate the digital signals received from the analog-to-digital converter 125.

In operation, the current source 130 may excite one or more of the light sources 105 by transmitting alternating pulses of fixed current to the light source 105. The light source 105 is illuminated (e.g., light source 105 excitation) when the current pulses exceed a minimum illumination level, and the light source 105 is turned off when the current pulse falls below the minimum illumination level. Therefore, the light generated by the light sources 105 pulses at the same frequency as the pulses output by the current source 130. The frequency of the pulses may be determined by the processor 135 or may be set to a predetermined value.

The light generated by the light source 105 may travel through a patient's body (e.g., tissue) and be received by the photodetector 110. Upon receiving the light from the light source 105, the photodetector 110 may output a current that may be converted to voltage by one or more of the trans-impedance amplifiers 120. The voltage output of the trans-impedance amplifier 120 may be continuously sampled by the analog-to-digital converter 125 and generate a digital output. The processor 135 may subtract the digital output received from the analog-to-digital converter 125 during the light source 105 excitation from the digital output from the analog-to-digital converter 125 during times when the light sources 105 are not emitting light to synchronously demodulate the output of the photodetectors 110. In order to achieve good signal to noise ratio, the signals from photodiodes may be over-sampled by the analog-to-digital converter 125. For example, the sampling frequency may be more than double the highest frequency of the voltage output of the trans-impedance amplifier 120. The analog-to-digital converter 125 may transmit multiple samples to the processor 135, and the processor 135 may average the multiple samples with a moving average filter or a cascade of moving averaging filters. By doing so, the processor 135 may remove interference from an interfering sensor 145, such as a pulse oximeter sensor, or ambient light.

Figure 2:
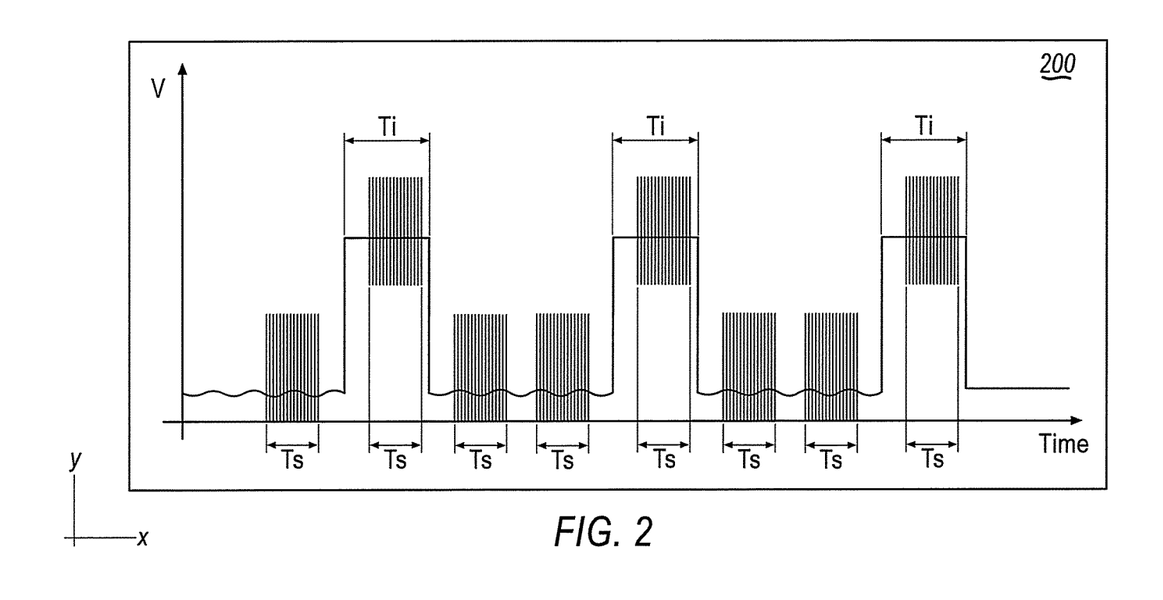
FIG. 2 is an exemplary time domain plot of an output of a trans-impedance amplifier of the tissue oximeter sensor.

FIG. 2 illustrates an exemplary graph 200 of the voltage output of the trans-impedance amplifier 120. The graph includes time represented on the x-axis and voltage represented on the y-axis. The time interval $T_i$ is the pulse duration, and the time interval $T_s$ is the sampling period. As illustrated in FIG. 2, the pulse is oversampled sixteen times with eight sampling periods $T_s$.

A high voltage signal indicates that the light source 105 is illuminated and the photodetector 110 is receiving the light generated by the light source 105. A lower voltage signal indicates that the light source 105 is off. However, the photodetectors 110 may receive ambient light or other interference when the light source 105 is off, which is represented by the fluctuating low voltage signal output by the trans-impedance amplifier 120.

To establish appropriate frequency response the oversampling data may be averaged by the processor 135 using a moving averaging filter or cascaded moving averaging filters. If the moving averaging filter is used, the averaging is equivalent to the filtering of the signal. The transfer characteristics (e.g., $H_N(f)$) of the moving average filter may be defined as follows:

$$H_N(f)=(1/N)*(1-z^N)/(1-z)=\sin(\pi fN/f_s)/N\sin(\pi f/f_s) \quad (1)$$

Where $f_s$ is the sampling frequency of the analog-to-digital converter 125, N is the oversampling number or constant that corresponds to the frequency of the interfering signal as discussed in further detail below, and $z=e^{(-j2\pi f/fs)}$. The processor 135 may apply the filter as defined in Equation (1), for example, to demodulate the signal received from the analog-to-digital converter 125. As illustrated in FIG. 2, the oversampling number N is sixteen and there are eight sampling periods $T_s$.

Figure 3:
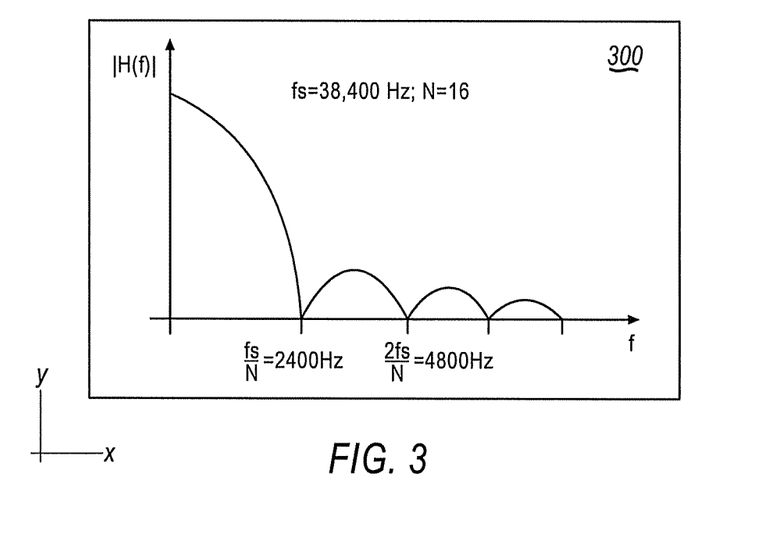
FIG. 3 is an exemplary frequency domain plot of a moving averaging filter that may be used to average multiple samples of an analog-to-digital converter of the tissue oximeter during demodulation.

FIG. 3 illustrates an exemplary frequency response 300 of the moving average filter as defined in Equation (1) where the sampling frequency $f_s$ is equal to 38,400 Hz. The frequency f is represented on the x-axis and the result of Equation (1) is represented on the y-axis. FIG. 3 shows that the filter defined by Equation (1) has multiple notches at the harmonic frequencies of $f_s$. For example, the harmonics occur where the frequency is equal to $f_s*M/N$, where M is an integer representing the number of the harmonic and N is the oversampling number (e.g., 16).

Figure 4:
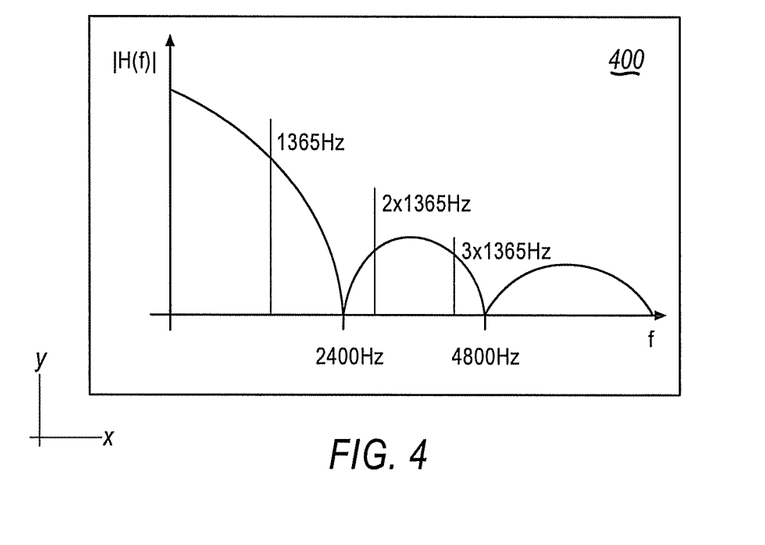
FIG. 4 illustrates an exemplary frequency response of the moving averaging filter used to average multiple samples of the analog-to-digital converter along with a spectrum of the interfering signal from the interfering sensor.

FIG. 4 illustrates an exemplary frequency response 400 where the frequency response of the filter defined by Equation (1) is plotted along with a spectrum of an interfering pulse oximeter signal. As illustrated, the frequency of the first harmonic of the interfering pulse oximeter signal is plotted as a single line at 1365 Hz. The pulse oximeter sensor may use rectangular pulses to excite the light source 105 so the high harmonics of the interfering signals may have a smaller amplitude than the first harmonic. The harmonics are represented by a series of bars with decreasing amplitude at frequencies defined by $M*f_i$, where M represents the number of the harmonic and $f_i$ is the frequency of the light pulses generated by the interfering sensor 145.

In Equation (1) above, the sampling frequency $f_s$ of the analog-to-digital converter 125 of the tissue oximeter 100 may be a fixed value defined by a clock within the processor 135. The over-sampling value N may define the efficiency of the demodulator needed to reduce the noise from the analog-to-digital converter 125 and the trans-impedance amplifier 120. The value of N may be varied to some degree without significantly affecting performance of the oximeter. For example, as illustrated in FIG. 4 the value of N may be defined as follows in Equation (2):

$$N=f_s*M/f_i, \quad (2)$$

To reduce interference, the interfering frequency $f_i$ and harmonics of the interfering frequency (e.g., represented by $M*f_i$) should fall into the notches of the moving average filter defined by Equation (1) as $H_N(f)$, reducing the interfering signal from, for example, the interfering pulse oximeter. However, as illustrated in FIG. 4, where the oversampling number N is equal to 16, the frequency $f_i$ of the interfering signal falls close to the peaks instead of the notches.

Figure 5:
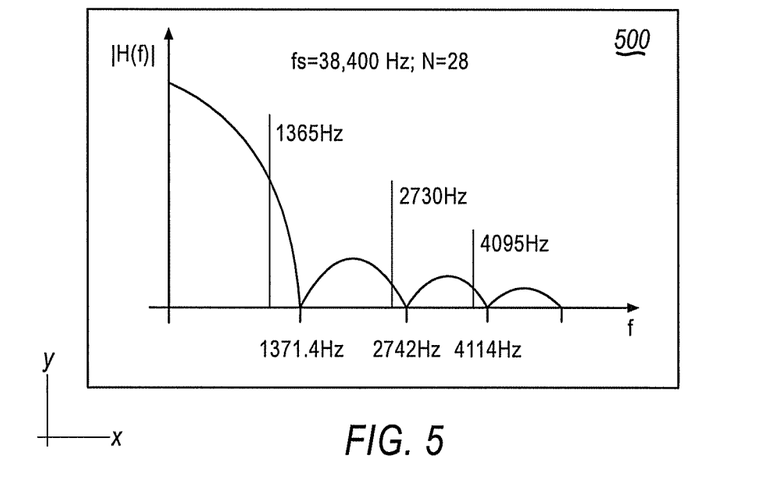
FIG. 5 illustrates an exemplary frequency response of a low pass filter that may be used reduce the effects of interference caused by the interfering sensor.

FIG. 5 illustrates another exemplary frequency response 500 where the frequency response of the filter defined by Equation (1) is plotted along with a spectrum of an interfering pulse oximeter signal. In the exemplary approach illustrated in FIG. 5, the oversampling number N is equal to 28 to move the interfering frequency $f_i$ and harmonics of the interfering frequency closer to the notches, resulting in the notch of the moving average filter defined by Equation (1) as $H_N(f)$ being located at 1371 Hz (e.g., $f_s/28=1371$ Hz), which places the notch close to the interfering frequency $f_i$, which as discussed above, may be 1365 Hz if the interfering sensor 145 is a pulse oximeter sensor. In this exemplary illustration, the oversampling number N may be adjusted to 29, moving the notches to 1324 Hz (e.g., $f_s/29=1324$ Hz), which surpasses the frequency of the interfering signal $f_i$ at 1365 Hz.

To place the notch of the filter at 1365 Hz the processor 135 may apply a weighted linear combination of two filters as defined in Equation 3 below:

$$H_a(f)=a*H_{28}(f)+(1-a)*H_{29}(f) \quad (3)$$

Figure 6:
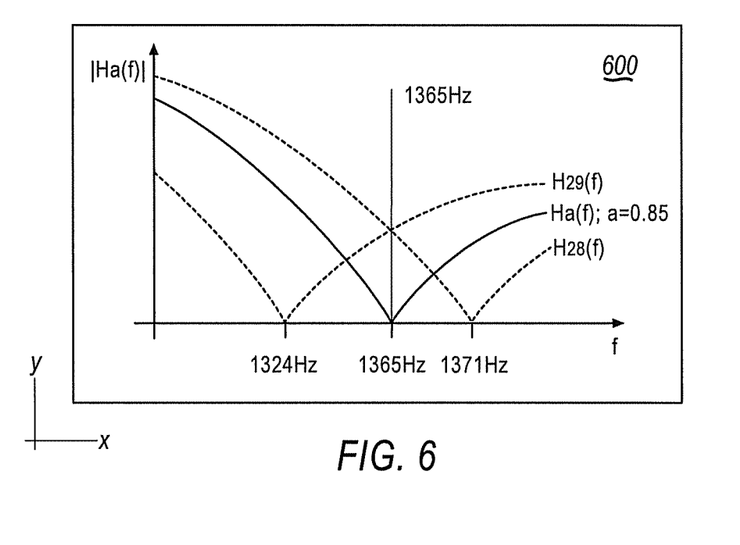
FIG. 6 illustrates an exemplary linear combination of the filters of FIG. 4 and FIG. 5.

In Equation (3), the value a is a constant between 0 and 1 (e.g., 0<a<1) representing weight. FIG. 6 represents the frequency response 600 of the exemplary filter defined by Equation (3) as $H_a(f)$ where a is equal to 0.85, which moves the notches of the tissue oximeter sensor 100 pulses to 1365 Hz to correspond to the frequency of the interfering signal. With the interfering pulse oximeter sensor signal at the notches of the harmonics of the pulses of the tissue oximeter sensor 100, the tissue oximeter sensor 100 is able to eliminate interference from the interfering sensor 145. Thus, the interfering pulse oximeter signal is invisible to the tissue oximeter 100.

The presented approach to reducing interference from interfering sensors 145, such as pulse oximeter sensors, includes selecting the oversampling number of the analog-to-digital converter 125 before decimation of the frequency of interfering light pulses from, for example, the pulse oximeter. Thus, the processor 135 of the tissue oximeter 100 may be configured to automatically determine the frequency of the light pulses of the interfering sensor 145.

Instead of the processor 135 automatically detecting the frequency of interfering light pulses, the tissue oximeter 100 may include an input device (not shown) that allows a user to manually input the type of interfering sensor 145 in use based on a brand name or the specifications of the interfering sensor 145. The processor 135 may prompt the user for this information and include a corresponding lookup table. Based on the information provided by the user, the processor 135 may access the lookup table and configure the tissue oximeter 100 to filter the interference using the methods previously described. The processor 135 may have a menu where the user can select the type of interfering sensor 145 in use by name brand or any other characteristic and automatically set the filter's parameters to remove interference from the interfering sensor 145. The filter can be activated upon a user request or automatically upon detection of interference.

In one exemplary approach, the tissue oximeter sensor 100 may use one or more of the photodetectors 110 to sample the pulse oximeter light pulses and automatically select the oversampling rate N of the filter so as to place the notch of the filter at the frequency measured by the photodetector 110 and eliminate interference. This may be done at the beginning of the monitoring period, periodically during monitoring, or may be triggered by the processor 135 based on detection of a high amplitude aliasing beat frequency caused by interference. It can also be performed on command by the user if or when the user wishes to place a pulse oximeter sensor near the tissue oximeter sensor 100.

In another exemplary approach, the tissue oximeter 100 may use only one of its multiple sensors to automatically select the oversampling rate N of the filter so as to place the notch of the filter exactly at the frequency measured and eliminate interference.

Figure 7:
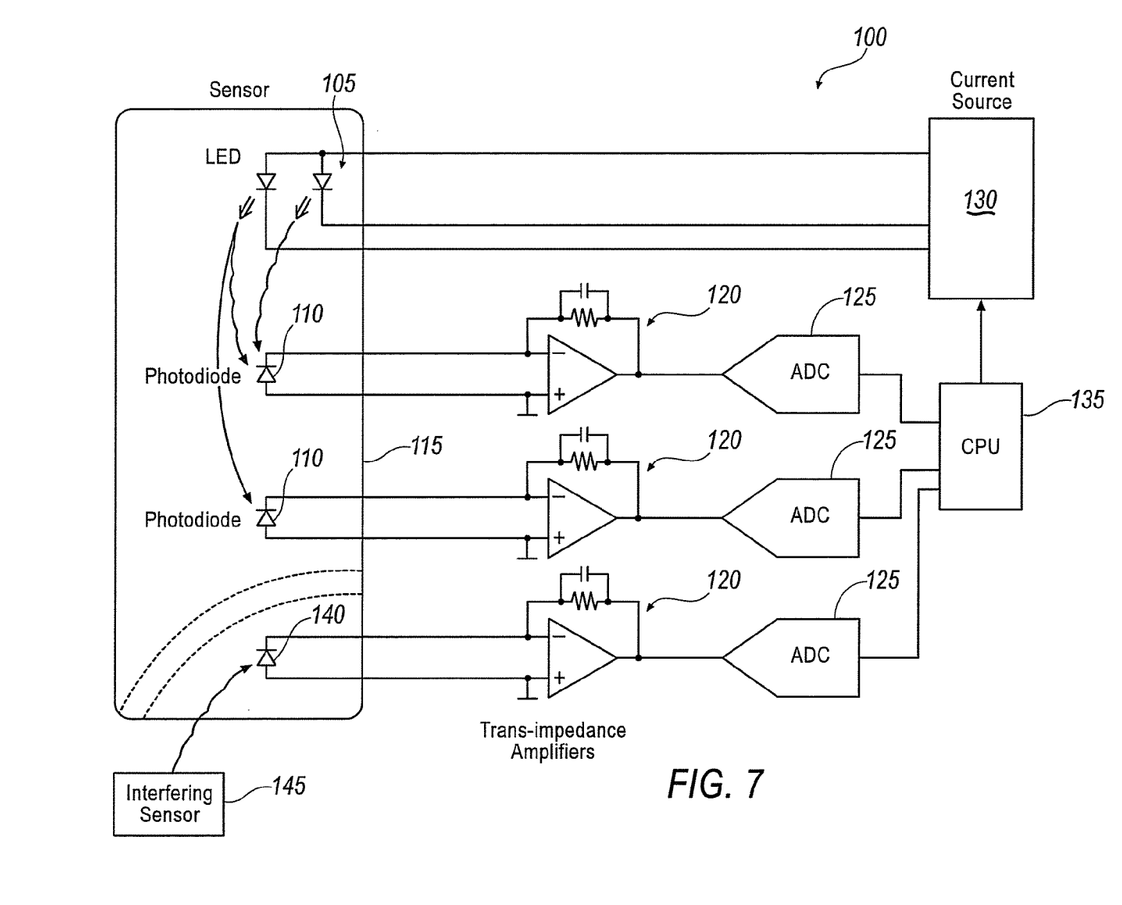
FIG. 7 illustrates an exemplary tissue oximeter sensor having a dedicated photodetector configured to detect interference from the interfering sensor.

Referring now to FIG. 7, alternatively, the tissue oximeter 100 may include the light sources 105 and photodetectors 110 disposed on the sensor pad 115, as well as trans-impedance amplifiers 120, analog-to-digital converters 125, current source 130, and processor 135 as discussed above with regard to FIG. 1. However, the tissue oximeter sensor 100 of FIG. 7 may further include a dedicated photodetector 140.

The dedicated photodetector 140 may be configured to detect interference from, for example, the light source of the interfering sensor 145. The dedicated photodetector 140 may include a photodiode and may be located on the same sensor pad 115 or a different sensor pad as the tissue oximeter sensor 100. For example, the dedicated photodetector 140 may be located near an edge of the sensor pad 115 as illustrated in FIG. 7, or located on a separate pad so that it may be placed near the pulse oximeter sensor. The dedicated photodetector 140 may be coupled to the processor 135 through a separate trans-impedance amplifier 120 and analog-to-digital converter 125. In operation, the dedicated photodetector 140 may be used to measure the frequency of the interfering pulses from the pulse oximeter and automatically select the oversampling number N of the filter so as to place the notch of the filter at the frequency measured by the dedicated photodetector 140 to eliminate interference.

Devices or monitors other than the pulse oximeter may also interfere with the tissue oximeter 100. For example, the interference may be electromagnetic instead of optical as previously described. For example, impedance pneumography is a technique that measures breathing rate by impressing a high-frequency sinusoidal current across conductive electrodes placed on a patient's chest. While impedance pneumography does not generate significant harmonics, the fundamental frequency may be in a range where it can cause interference with the tissue oximeter 100. Likewise, certain electrocardiograph or electroencephalograph monitors may impress a high-frequency sinusoidal current across conductive electrodes placed on the patient to allow measurement of electrode impedance. Additionally, other patient monitors may generate significant electromagnetic interference during operation such as a transcranial Doppler ultrasonic monitor. In each of these cases, the system and techniques described here may be used to reduce or eliminate unwanted interference with the tissue oximeter 100.

Instead of using fixed value for the oversampling number N and the constant a, the processor 135 may be configured to vary the oversampling number N and constant a in a random fashion within predetermined intervals. Random variations the parameters of $H_a(f)$ may introduce a random amplitude modulation of the filter residual. Such modulation will spread the peak frequency of the residual into random noise, producing the random noise instead of the high amplitude alias of the interfering signal from, for example, the pulse oximeter.

Moreover, instead of reducing interference from one or more pulse oximeters, the same techniques may be used to reduce interference from one or more other tissue oximeters on the patient that employ pulses with higher repetition. For example, one tissue oximeter may use multiple channels with different pulse repetition frequencies.

Further, instead of the moving averaging filter or the cascaded moving averaging, a linear combination of the cascaded moving averaging filters may be used.

The above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

The invention claimed is:

1. A system comprising:
a light source;
at least one photodetector in optical communication with said light source; and
a processor in communication with said photodetector and configured to output a signal independent of an interfering signal caused by an interfering sensor; and
an analog-to-digital converter in communication with said processor and configured to digitize a signal from said photodetector by oversampling and output oversampling data to said processor;
wherein said processor includes an averaging filter in communication with said analog-to-digital converter and configured to average the oversampling data received from said analog-to-digital converter prior to decimation based on an oversampling number associated with a sampling frequency of the analog-to-digital converter and a frequency of the interfering signal, wherein the oversampling number defines notches in a frequency response of the filter at one or more frequencies associated with the interfering signal.

2. A system as set forth in claim 1, wherein said averaging filter includes a notch before decimation, wherein said notch has a frequency that corresponds to a frequency of the interfering signal.

3. A system as set forth in claim 1, wherein said processor is configured to apply a weighted linear combination to the oversampling data.

4. A system as set forth in claim 3, wherein the weighted linear combination includes at least one of a weight and an oversampling number that are varied randomly.

5. A system as set forth in claim 1, wherein said photodetectors are configured to receive the interfering signal and wherein said processor is configured to measure a frequency of the interfering signal.

6. A system as set forth in claim 1, wherein at least one of said photodetectors is configured to detect the interfering signal from the interfering sensor.

7. A tissue oximeter sensor comprising:
a light source;
a photodetector in optical communication with said light source; and
a processor in communication with said photodetector and configured to output a signal representing oxygen saturation independent of an interfering signal caused by an interfering source, wherein the processor is configured to:
 select an oversampling number based on a sampling frequency and a frequency of the interfering signal, wherein the oversampling number defines notches in a frequency response of a filter at one or more frequencies associated with the interfering signal, and
 reduce the interfering signal in accordance with the oversampling number.

8. A sensor as set forth in claim 7, an analog-to-digital converter in communication with said processor and configured to digitize a signal from said photodetector by oversampling and further configured to output oversampling data to said processor.

9. A sensor as set forth in claim 8, wherein said processor includes an averaging filter in communication with said analog-to-digital converter and configured to average oversampling data received from said analog-to-digital converter.

10. A sensor as set forth in claim 9, wherein said processor is configured to apply a weighted linear combination to the oversampling data.

11. A sensor as set forth in claim 10, wherein the weighted linear combination includes at least one of a weight and the oversampling number.

12. A sensor as set forth in claim 11, wherein the weight corresponds to a frequency of the interfering signal.

13. A sensor as set forth in claim 7, wherein said light source and said photodiode are disposed on a sensor pad.

14. A sensor as set forth in claim 7, wherein said light source is disposed on a first sensor pad and said photodetector is disposed on a second sensor pad.

15. A sensor as set forth in claim 7, wherein said photodetector is configured to detect a frequency of the interfering signal.

16. A system comprising:
a tissue oximeter sensor having a light source in optical communication with a photodetector and a processor in communication with said photodetector;
an interfering sensor configured to output an interfering signal having a frequency;
wherein said tissue oximeter is configured to output a signal independent of the interfering signal output by said interfering sensor by:
 selecting an oversampling number based on a sampling frequency and the frequency of the interfering signal, wherein the oversampling number defines notches in a frequency response of a filter at one or more frequencies associated with the interfering signal, and
 reducing the interfering signal in accordance with the oversampling number.

17. A system as set forth in claim 16, wherein said tissue oximeter sensor includes an analog-to-digital converter in communication with said processor and configured to digitize a signal from said photodetector by oversampling and further configured to output oversampling data to said processor.

18. A system as set forth in claim 17, wherein said processor includes an averaging filter in communication with said analog-to-digital converter and configured to average oversampling data received from said analog-to-digital converter.

* * * * *